United States Patent [19]

Hamill et al.

[11] 4,087,603

[45] May 2, 1978

[54] ANTIFUNGAL ANTIBIOTICS

[75] Inventors: Robert L. Hamill; Ramakrishnan Nagarajan, both of Indianapolis, Ind.

[73] Assignee: Eli Lilly and Company, Indianapolis, Ind.

[21] Appl. No.: 726,725

[22] Filed: Sep. 27, 1976

[51] Int. Cl.² ............................................. C07H 19/16
[52] U.S. Cl. ...................................... 536/26; 424/181; 544/277
[58] Field of Search ........................... 536/26; 260/252

[56] References Cited

U.S. PATENT DOCUMENTS 3,758,681  9/1973  Hamill et al. ..................... 424/118

*Primary Examiner*—Paul M. Coughlan, Jr.
*Attorney, Agent, or Firm*—William B. Scanlon; Everet F. Smith

[57] ABSTRACT

5'-Deoxy-5'-(3'-aminopiperidin-2-one-6-yl)adenosine and 5'-deoxy-5'-(1-amino-4-ureido-4-carboxyamidobutyl)-adenosine and the pharmaceutically acceptable acid addition salts thereof are antifungal antibiotics active vs. systemic infections produced by culturing *Streptomyces griseolus* NRRL 3739 and are isolated from the broth and obtained pure via chromatography over cationic resin.

3 Claims, No Drawings

ANTIFUNGAL ANTIBIOTICS

BACKGROUND OF THE INVENTION

This invention relates to antifungal antibiotics. In particular, this invention relates to adenine containing antibiotic compounds which are effective in vivo antifungal agents.

Although many antibiotics, for example, the penicillins and the cephalosporins, are highly effective in the treatment of bacterial infections, more effective agents in the treatment of systemic fungal infections are needed. Accordingly, the search for antibiotics effective in the treatment of systemic fungal infections of man and animals is the subject of a continuing research effort.

The antifungal agents of this invention were discovered as minor factors occurring in the fermentation broth of *Streptomyces griseolus* NRRL 3739. This microorganism is used in the production of the known antifungal antibiotic A-9145 as described by U.S. Pat. No. 3,758,681 issued Sept. 11, 1973. Following the discovery of the antibiotic A-9145, continuing development of isolation procedures for the antibiotic led to the discovery of the previously unrecognized minor factors which form the subject of this invention. The detection of the presence of the antifungal factors described herein was rendered difficult because of their low order of antibacterial and antifungal activity in standard in vitro tests.

In contrast to the antibiotic A-9145 which is active both in vitro and in vivo, the antifungal agents provided by this invention display minimal antifungal activity in vitro but are effective antifungal agents in vivo.

DETAILED DESCRIPTION

The antifungal antibiotics provided by this invention are represented by the following structural formulas I and II.

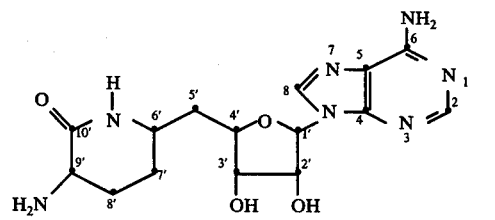

I

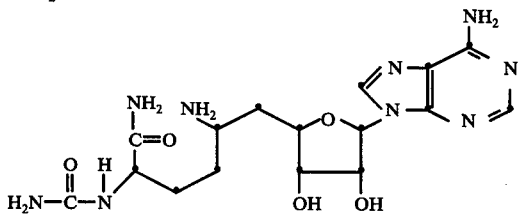

II

As shown in the above structural formulas, the compounds of this invention can be conveniently characterized as 5'-deoxy-5'-substituted adenosines. Accordingly, the compound of the formula I can be named 5'-deoxy-5'-(3-aminopiperidin-2-one-6-yl)adenosine, while the compound of formula II can be named 5'-deoxy-5'-(1-amino-4-ureido-4-carboxyamidobutyl)adenosine. The compound of the invention represented by the above formula I is further characterized by the amino-substituted six-membered lactam ring substituent in the 5'-position of the adenosine molecule. The structurally related compound of the formula II has an open-chain butyl substituent substituted with an amino group, a ureido group, and the carboxamido group as shown.

For convenience, the compounds of the formulas I and II are named informally as derivatives of adenosine represented by the following formula.

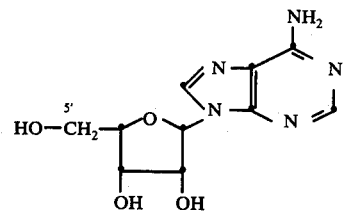

In the above formula, the 5'-position is indicated to show 5'-deoxy adenosine naming system used above.

The antifungal compounds of this invention are isolated along with the known antibiotic A-9145 from the fermentation medium of *Streptomyces griseolus* NRRL 3739.

It has yet to be determined whether the antifungal compound I of this invention is a true metabolite of the above-named microorganism or is an artifact arising during the isolation procedure.

Since its discovery, the antibiotic A-9145 has been further purified and its structure determined by its spectral and analytical characteristics as well as by mass spectroscopy. The structure of A-9145 is as follows.

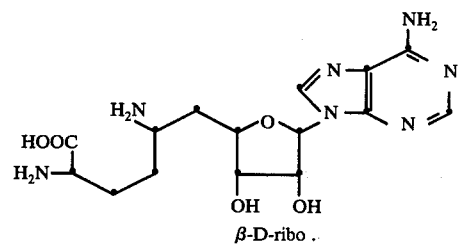

β-D-ribo.

By following the same informal nomenclature employed above in the naming of compounds of formulas I and II, A-9145 is named 5'-deoxy-5'-(1,4-diamino-4-carboxybutyl)adenosine. As indicated in the above structural formula, the furanose ring has the β-ribo stereochemistry while the configuration of the amino acid center is L.

Antibiotic A-9145 is the most prevalent substance produced in the fermentation of *S. griseolus* NRRL 3739. The second most abundant substance produced in the fermentation, although in minor quantities, is "dehydro A-9145" represented by the following formula.

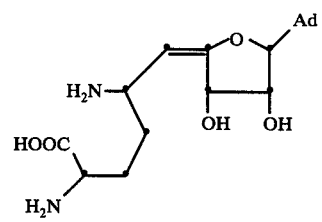

"Dehydro A-9145" was discovered along with the antifungal compounds I and II during the separation of A-9145 by the chromatographic techniques described herein. Because of the close physical and structural similarities of A-9145, "dehydro A-9145" and compounds I and II, the occurrence of these minor factors in the S. griseolus fermentation went unrecognized during the discovery of A-9145.

The preparation of A-9145 by culturing S. griseolus NRRL 3739 in a nutrient culture medium under submerged aerobic fermentation conditions is described in U.S. Pat. No. 3,758,681 issued Sept. 11, 1973 and by Hamill, et al., J. Antibiotics, 26:463–465, 1973. The antifungal compounds I and II provided by this invention are obtained during the recovery and isolation of A-9145 from the filtered fermentation broth. The isolation of the compounds I and II can be carried out by chromatography of the filtered fermentation broth over a cationic exchange resin or, alternatively, from a crude preparation of A-9145 previously recovered from the filtered fermentation broth. The chromatography in either case is carried out by stepwise gradient elution or by the continuous gradient elution technique. In each instance, the newly discovered antifungal compounds of this invention are separable from A-9145 and "dehydro A-9145" by eluting the cation exchange resin with ammonium hydroxide having a normality of between about 0.05 N and 0.2 N.

Cationic exchange resins which are useful in the isolation of compounds (I and II) are the commercially available polystyrene-sulfonic acid resins for example, Dowex 50 $w \times 2$ (Dow Chemical Company), and the acryliccarboxylic acid resins such as Bio Rex 70 (Bio-Rad Laboratories) and Amberlite IRC-50 (Rohm & Haas Co.). In order to separate the compounds of this invention from the antibiotic A-9145, the cationic resins are employed in the ammonium cycle.

When isolating the components from the fermentation broth, the broth is first filtered with the help of a filter aid and the filtered broth is added to a column containing the cationic exchange resin in the ammonium cycle. The column is then washed with water to remove impurities and the compounds are eluted from the column with ammonium hydroxide having a normality between about 0.05 N and about 0.2 N. Alternatively, the compounds I and II can be separated from a crude preparation of A-9145 which has been previously isolated from a filtered fermentation broth as described in U.S. Pat. No. 3,758,681. For example, as described therein, the filtered fermentation broth is passed over a cationic exchange resin in the hydrogen cycle and the resin is first washed with water to remove impurities. Thereafter, A-9145 is eluted from the resin with a dilute mineral acid such as 0.05 N sulfuric acid. The eluate fractions containing antibiotic activity are combined and neutralized with a base preferably barium hydroxide. Thereafter, the neutralized combined eluate is concentrated and the concentrate diluted with a water miscible organic solvent such as methanol to precipitate the crude A-9145. The crude preparation is then dissolved in a minimum amount of water and the solution is passed over a column packed with Bio Rex 70 (ammonium cycle) prepared in water. The A-9145 "dehydro A-9145", compounds I and II, and other minor factors are then eluted from the column with dilute ammonium hydroxide by the gradient elution technique as follows. A first vessel containing 0.3 N ammonium hydroxide is allowed to feed dropwise into a second vessel containing water while the latter feeds dropwise onto the column. Compound I is contained in the early eluate followed by fractions containing other minor factors. Next, fractions containing the major factor A-9145 are collected followed by fractions containing A-9145 and "dehydro A-9145". Compound II is collected in the last fractions off the column.

The early eluate fractions rich in compound I are combined and chromatographed over Bio-Rex-70 ($NH_4^+$) using about 0.05 N ammonium hydroxide to elute only compound I.

The late eluate fractions rich in compound II are likewise combined and chromatographed over the same resin. The resin is first eluted with about 0.05 N ammonium hydroxide to elute impurities and then with 0.2 N ammonium hydroxide to elute compound II.

The course of the chromatographic separation can be followed by carrying out thin layer chromatograms (TLC) on the collected fractions. A suitable TLC system employs silica gel coated plates and a chloroform:methanol:ammonium hydroxide (1:3:1, v:v:v) as the solvent system. The location of the various compounds on the chromatogram is determined initially with UV light and then development of the spots thus located with sodium hypochlorite:ethanol:p-phenylenediamine spray reagent.

Another suitable TLC system for detecting the presence of the factors comprises silica gel coated plates and development with 15 percent aqueous sodium chloride.

Rf values for the respective factors in the two TLC systems are as follows:

| Compound | Rf (CMA)[1] | Rf (NaCl)[2] |
|---|---|---|
| II | 0.1 | 0.60 (moves with A-9145) |
| "dehydro A-9145" | 0.45 | 0.66 |
| A-9145 | 0.56 | 0.60 (moves with II) |
| I | 0.69 | 0.45 |

[1]Chloroform:methyl alcohol:ammonium hydroxide
[2]15 percent aq. NaCl

All fractions shown by TLC to contain the same substance were combined and evaporated to dryness to obtain the compound as a solid residue. Antifungal compound I is obtained crystalline by crystallizing the residue from a suitable solvent mixture such as methanol and acetone. Compound II has been obtained as an amorphous solid.

The antifungal compound I melts at about 226°–228° C. dec., is highly soluble in water and sparingly soluble in methanol, ethanol and acetone. The ultraviolet absorption spectrum of compound I shows the characteristic adenine chromophore.

UV ($H_2O$) 259 nm ($\epsilon = 15,400$) 1st transition; 200 nm ($\epsilon = 38,900$) 2nd transition Potentiometric titration of compound I in 80% methyl cellosolve gave an initial pH of 9.0 and pKa of ca. 2.5 and 7.4.

The nuclear magnetic resonance spectrum of compound I in dimethyl sulfoxide (DMSO) and in deuterium oxide is as follows, wherein the position of the proton is indicated with reference to formula I above.

| Position | $^1$H NMR DMSO | $D_2O$ |
|---|---|---|
| 2 | 8.16 | 8.08 |
| 8 | 8.30 | 8.15 |
| 6-$NH_2$ | 7.25 | — |
| 1' | 5.86 | 5.93 |
| 2' | 4.67 | 4.70 |
| 3' | 4.03 | 4.20 |
| 4' | 4.03 | 4.20 |
| 5' | 1.90 | 1.85 |

-continued

| Position | ¹H NMR | |
| --- | --- | --- |
| | DMSO | D₂O |
| 6' | 3.42 | 3.55 |
| 7' | 1.70 | 1.85 |
| 8' | 1.90 | 1.85 |
| 9' | 3.05 | 3.30 |
| 6'-NH | 7.76 | — |

The $^{13}C$ nuclear magnetic resonance spectrum of compound I in dimethyl sulfoxide is as follows.

| $^{13}$C NMR (DMSO) | |
| --- | --- |
| Position | |
| 2 | 152.7 |
| 4 | 149.4 |
| 5 | 119.3 |
| 6 | 156.1 |
| 8 | 140.1 |
| 1' | 88.1 |
| 2' | 73.9* |
| 3' | 72.9* |
| 4' | 81.1 |
| 5' | 40.1 |
| 6' | 48.9 |
| 7' | 26.3* |
| 8' | 25.8* |
| 9' | 50.7 |
| 10' | 173.8 |

*Assignment interchangeable

The antifungal compound of this invention represented by the above formula II is likewise highly soluble in water and melts at about 195°–198° C. (dec). Potentiometric titration of compound II in 66% dimethylformamide gave pKa values of <4.0 and 9.3.

The ultraviolet absorption spectrum of compound II in water showed absorption at 260 nm ($\epsilon$ = 10,750).

The 100 MHz NMR spectrum of compound II in 100% deuterium oxide as determined in a HA100 Varian spectrometer gave the following characteristics:

8.15δ (1H, s), 8.05 (1H, s), 5.94 (1H, d, J = 5Hz), 4.78 (1H, m), 4.21 (2H, m), 3.53 (1H, m), 3.35 (1H, m), 2.00 (2H, m), and 1.65 (4H, m).

δ in ppm., $s$ = singlet, $d$ = doublet, and $m$ = multiplet.

The structures of the antifungal compounds of this invention were determined by a study of the spectral and analytical properties of the compounds. The field desorption mass spectra were used in determining the molecular weights which along with the elemental analysis, titration, ultraviolet spectrum, nuclear magnetic resonance spectra, and amino acid analysis led to the assigned structures. The mass spectra of compound I gave an m/e (molecular ion) of 363. Further, analysis of numerous field-desorption mass spectral runs of compounds I and II at varying emitter currents demonstrated molecular weights of 363 for compound I and 423 for compound II.

As previously mentioned, the compounds of this invention are effective systemic antifungal agents. When administered orally or parenterally, the antifungal compounds of this invention are effective in combatting systemic fungal infections for example, *Candida albicans* systemic infections. The in vivo antifungal activity of compounds I and II is demonstrated in mice infected with *C. albicans* A-26. The tests in mice were carried out in the following manner. Two groups of mice, one a control group, were exposed to a sub-lethal dose of X-irradiation 24 hours prior to infection with *C. albicans* A-26. The mice were infected by intravenous administration of *C. albicans* cells. The average effective dose, $ED_{50}$, for compound I, was 38 mg./kg. sc. while that of compound II was about 21 mg./kg. sc.

When antifungal compound I was administered to mice, at a dose of about 1000 mg./kg. no acute toxicity was observed. With compound II no acute toxicity was observed at a dose of 400 mg./kg.

The antifungal agents of this invention are basic compounds which form acid addition salts. Acid addition salts formed with pharmaceutically acceptable acids can be used in formulations suitable for administration of the antifungal agents. For example, salts can be formed with the inorganic acids such as hydrochloric acid, hydrobromic acid, sulfuric acid, and phosphoric acid. Organic carboxylic acids which are suitable in the preparation of pharmaceutically acceptable salts include for example, the monocarboxylic acids such as acetic acid, propionic acid, benzoic acid, and substituted benzoic acids such as anisic acid and salicyclic acid, the dicarboxylic acids such as maleic acid, fumaric acid, as well as citric acid and tartaric acid. The alkyl and aryl sulfonic acids such as methanesulfonic acid, ethanedisulfonic acid, p-toluenesulfonic acid, and naphthalenesulfonic acid also form salts.

The antifungal compounds of this invention and the pharmaceutically acceptable non-toxic acid addition salts thereof can be administered parenterally or orally at a non-toxic dose of between about 75 mg./kg. to about 500 mg./kg.

The antifungal agents I and II can be administered by the parenteral route for example, subcutaneously or intravenously as an isotonic solution as for example, in isotonic saline or in sterile distilled water. For oral administration, the antibiotics can be formulated with an inert pharmaceutically acceptable carrier for incorporation in capsules, tablets, or as a lozenge. Alternatively, the antifungal agents can be formulated as aqueous suspensions as a water insoluble salt form.

As noted previously, the compounds I and II are produced in minor amounts in the fermentation of *S. griseolus*. A-9145 is the predominant product obtained in the fermentation and commonly comprises about 75 to 85 percent of recovered antibiotic substance. "Dehydro A-9145" commonly is present in amounts approximating 10 percent of the recovered antibiotic substance. Other minor factors are detected in the eluate of the chromatograms used to obtain compounds I and II or A-9145; however, they are present in such minor amounts as to make their recovery and identification unrewarding.

With the discovery of antifungal compound I and the subsequent determination of its structure, it was also discovered that compound I could be prepared with the more abundant A-9145.

Accordingly, in a further aspect of this invention, there is provided a process for the conversion of the known antifungal A-9145 to the antifungal agent I of this invention. According to this process, A-9145 is heated in an aqueous or non-aqueous inert solvent at a temperature between about 25° and 80° C. and the product I is recovered from the mixture. The process is illustrated by the following reaction scheme.

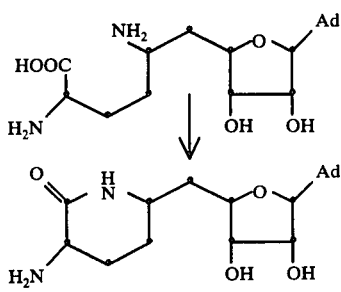

wherein Ad refers to the adenine moiety of both A-9145 and antifungal agent I.

As shown in the above reaction scheme, the carboxylic acid group associated with the amino acid moiety of A-9145 cyclizes with the available primary amino group to form the six-membered amino substituted lactam ring.

Inert solvents which can be employed in the process include water, the lower alcohols such as methanol, ethanol, isopropanol, and n-butanol, the ethers such as tetrahydrofuran and dioxane, esters such as ethyl acetate, amyl acetate, and the like. The process is preferably carried out in anhydrous methanol or anhydrous ethanol. Yields ranging between 55 and 65% are obtained in these dry solvents. In an aqueous medium such as in a wet alcohol or in water itself, lower yields of the product, compound I, are obtained.

TLC assay of the reaction indicates an equilibrium reaction which when carried out in water or an aqueous solvent favors A-9145. When carried out in an anhydrous solvent compound I is favored. A second product, as yet unidentified, occurs in the mixture as a minor component when the reaction of A-9145 I is heated for extensive periods, in a dry solvent. Evidence indicates that the second product is a dimer of A-9145, formed by the loss of two moles of water to form a diketopiperazine.

In a preferred embodiment of the process, A-9145 is suspended or dissolved in methanol (in which it is partially soluble) and the solution or suspension is heated at the reflux temperature for betweeen 24 and 78 hours. Preferably, the reaction is heated at the reflux temperature for about 72–78 hours and thereafter the solvent is removed by evaporation. The white residual product mixture is dissolved in a minimum amount of water by heating the suspension and thereafter the solution is cooled to a temperature of about 5° to about 15° C. The product, antifungal compound I, crystallizes from the cold solution and is filtered, washed with dry methanol, and dried.

EXAMPLE 1

Spores of *Streptomyces griseolus* strain NRRL 3739 are inoculated on a nutrient agar slant having the following composition:

| Ingredient | Weight (g.) |
|---|---|
| Dextrin | 10 |
| Soybean flour | 15 |
| Nadrisol[1] | 2 |
| Blackstrap molasses | 2 |
| CaCO$_3$ | 1 |
| Agar | 25 |
| Deionized water (Q.S. to a volume of one liter) | |

[1]National Distiller's Products Co.

The slant is incubated for 7 days at a temperature of 30° C. The mature slant culture is preserved by lyophilization in calf serum.

One lyophilized pellet is used to inoculate 50 ml. of a sterile vegetative growth medium having the following composition:

| Ingredient | Weight (g.) |
|---|---|
| Glucose | 10 |
| Dextrin | 30 |
| Soybean meal | 15 |
| Amber BYF 300[1] | 5 |
| Calcium carbonate | 2 |
| Blackstrap molasses | 5 |
| Water, q.s. to make one liter | |

[1]Amber BYF 300, Amber Laboratories, Juneau, Wisconsin.

The inoculated vegetative medium is grown for 30 hours at 30° C. with constant shaking on a rotary shaker at 250 r.p.m. to produce the vegetative form of the organism. A second seed stage, 200 ml. in a 2-liter flask, is then inoculated from the first stage. After an additional 24-hour incubation period under the same conditions of temperature and agitation, this inoculum is then employed to inoculate a sterile production culture medium having the following composition. The percentages shown are expressed on a weight-per volume basis:

| Ingredient | Percent |
|---|---|
| Cottonseed oil | 3.0 |
| L-tyrosine | 0.362 |
| Soybean meal (grits) | 1.5 |
| CoCl$_2$ . 6H$_2$O | 0.00025 |
| Calcium carbonate | 0.2 |
| Deionized water added to a volume of 100 liters | |

The inoculated culture medium contained in a 165-liter fermentation tank is allowed to ferment at a temperature of about 30° C. Throughout the fermentation period the medium is stirred at 200 r.p.m. and aerated with sterile air in an amount of about 0.2 volume of air per volume of culture medium per minute. The fermentation is allowed to continue for about 7 days, during which time the culture medium gradually decreases in pH from an initial level of about pH 7.4 to about pH 6.9.

The whole fermentation broth from two fermentations carried out as described above were combined and filtered with the aid of 3 percent Hyflo Super-Cel and 124 l. of the filtrate were applied to a chromatography column containing 8 l. of Amberlite IRC-50 (NH$_4$$^+$) resin. The column was washed with 100 l. of water and was then eluted with a continuous gradient provided by a 50 l. reservoir of 0.3 N ammonium hydroxide feeding into a 50 l. reservoir of water, the latter feeding the column. Multiple one-liter fractions were collected and the elution was monitored by TLC. Fractions 11–14 were rich in compound I and were combined and concentrated in vacuo to 30 ml. The concentrate was eluted with 60 ml. of methyl alcohol and 300 ml. of acetone. Compound I contaminated with A-9145 and other minor impurities precipitated, was filtered, washed with acetone, and dried to yield 1.44 g. of impure I.

Fractions 15–18 contain mostly A-9145 while fractions 19–26 contained A-9145, "dehydro A-9145" and compound II.

Fractions 27–66 containing compound II were combined and evaporated under reduced pressure to a 10 ml. concentrate. The concentrate was diluted with 20 ml. of methyl alcohol and 180 ml. of acetone to precipitate impure II. The precipitate was filtered, washed with acetone, and dried to yield 649 mg. of impure compound II.

The impure compound I (1.40 g.) obtained off the column as described above was dissolved in 20 ml. of water, and the solution was applied to a column containing 400 ml. of Bio-Rex 70 ($NH_4^+$) 100–200 mesh resin. The column was washed with 500 ml. of water and then was eluted with 0.05 N ammonium hydroxide. Multiple 15 ml. fractions were collected. Fractions 22–30 containing only compound I (TLC) were combined and concentrated in vacuo to 15 ml. The concentrate was diluted with 30 ml. of methyl alcohol and 150 ml. of acetone to precipitate compound I. The precipitate of I was filtered and dried to yield 350 mg. of pure I.

Two grams of impure compound II (obtained by accumulating impure II from several chromatograms run as described above) were dissolved in 20 ml. of water and the solution was applied to a column containing 440 ml. of Bio-Rex 70 ($NH_4^+$) 100–200 mesh resin. The column was washed with 50 ml. of water and elution was started with 0.05 N ammonium hydroxide. Multiple 15 ml. fractions of eluate were collected. After 295 fractions all of the A-9145 and other impurities had been eluted (TLC) and the eluting agent was changed to 0.2 N ammonium hydroxide. Fractions 324–342 contained compound II and were combined and evaporated to a 10 ml. concentrate. The concentrate was diluted with 20 ml. of methyl alcohol and 100 ml. of acetone to precipitate II. The precipitate was filtered and dried to yield 982 mg. of pure II.

EXAMPLE 2

Preparation of I with A-9145

A solution of 10.175 g. of A-9145 (0.0267 M) in 1.5 l. of absolute methyl alcohol (AR grade methyl alcohol dried over molecular sieve) was refluxed for 3.5 days. The reaction solution was evaporated to dryness and the residue of reaction product mixture was dissolved in the minimum amount of water with heating on the steam bath. The solution was filtered and refrigerated. On standing in the cold a crystalline precipitate formed and was filtered to yield 6.02 g. of compound I. The filtrate was allowed to stand in the cold and yielded a second crop of crystals which were filtered and dried. Yield, 175 mg. The second crop material appeared to be the diketopiperazine formed with A-9145.

We claim:
1. A compound in substantially pure form selected from the group consisting of

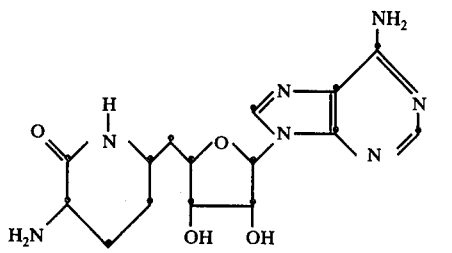

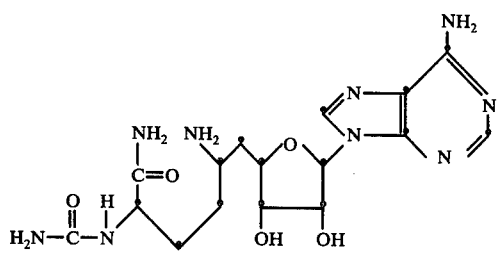

and the pharmaceutically acceptable, non-toxic acid addition salts thereof.

2. The compound of claim 1 of the formula

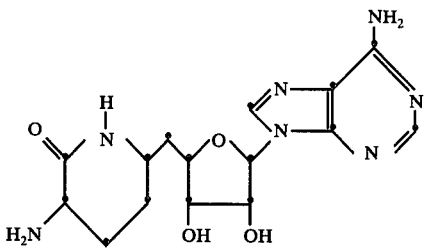

3. The compound of claim 1 of the formula

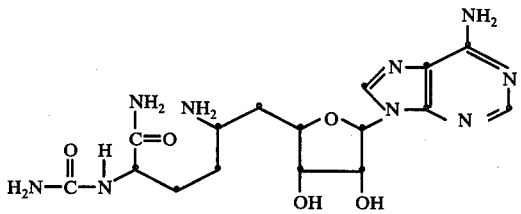

* * * * *